United States Patent
Rousseau et al.

(10) Patent No.: US 10,444,505 B2
(45) Date of Patent: Oct. 15, 2019

(54) HEAD MOUNTED DISPLAY DEVICE

(71) Applicant: Essilor International, Charenton-le-Pont (FR)

(72) Inventors: Denis Rousseau, Charenton-le-Pont (FR); Denis Cohen Tannoudji, Charenton-le-Pont (FR); Thierry Villette, Charenton-le-Pont (FR); Coralie Barrau, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/565,653

(22) PCT Filed: Apr. 11, 2016

(86) PCT No.: PCT/EP2016/057894
§ 371 (c)(1),
(2) Date: Oct. 10, 2017

(87) PCT Pub. No.: WO2016/162554
PCT Pub. Date: Oct. 13, 2016

(65) Prior Publication Data
US 2018/0074322 A1  Mar. 15, 2018

(30) Foreign Application Priority Data
Apr. 10, 2015 (EP) .................................. 15305531

(51) Int. Cl.
*G02B 27/01* (2006.01)
*A61N 5/06* (2006.01)
(Continued)

(52) U.S. Cl.
CPC ....... *G02B 27/0172* (2013.01); *A61N 5/0618* (2013.01); *G02B 27/0093* (2013.01);
(Continued)

(58) Field of Classification Search
CPC .. G02B 27/10; G02B 27/017; G02B 27/0081; G02B 27/0093; G02B 27/126;
(Continued)

(56) References Cited

U.S. PATENT DOCUMENTS

| 5,923,398 A | 7/1999 | Goldman |
| 9,019,614 B2 * | 4/2015 | DeVaul ................ G02B 3/0006 359/626 |

(Continued)

FOREIGN PATENT DOCUMENTS

WO   2010076706 A1   7/2010

OTHER PUBLICATIONS

International Search Report and Written Opinion for PCT/EP2016/057894 dated Jun. 9, 2016.

*Primary Examiner* — Sultan Chowdhury
(74) *Attorney, Agent, or Firm* — Oblon, McClelland, Maier & Neustadt, L.L.P.

(57) ABSTRACT

A head mounted display device comprising:
 a light emitting source,
 an optical waveguide adapted to collect light emitted from the light emitting source and to guide the collected light to the eye of a wearer when the head mounted display device is being worn by the wearer,
 a controller device adapted to control the emitted spectrum and/or radiance and/or light level emitted by the light emitting source.

19 Claims, 1 Drawing Sheet

(51) Int. Cl.
*G02B 27/00* (2006.01)
*G02B 27/09* (2006.01)
*G02B 27/10* (2006.01)
*A61B 18/00* (2006.01)
*G02C 7/08* (2006.01)

(52) U.S. Cl.
CPC ....... *G02B 27/017* (2013.01); *G02B 27/0977* (2013.01); *G02B 27/10* (2013.01); *A61B 2018/00642* (2013.01); *A61N 2005/063* (2013.01); *A61N 2005/0626* (2013.01); *A61N 2005/0648* (2013.01); *A61N 2005/0651* (2013.01); *G02B 2027/0178* (2013.01); *G02C 7/086* (2013.01); *G02C 2202/10* (2013.01); *G02C 2202/24* (2013.01)

(58) Field of Classification Search
CPC .............. G02B 27/141; G02B 27/0172; G02B 27/0977; G02B 2027/014; G02B 2027/0118; G02B 2027/0138; G02B 2027/0178

See application file for complete search history.

(56) References Cited

U.S. PATENT DOCUMENTS

| | | | | |
|---|---|---|---|---|
| 2007/0091445 | A1* | 4/2007 | Amitai | G02B 6/0056 359/630 |
| 2010/0149073 | A1* | 6/2010 | Chaum | G02B 27/0093 345/8 |
| 2011/0164294 | A1* | 7/2011 | Shimizu | G02B 27/0172 359/13 |
| 2014/0043591 | A1* | 2/2014 | Kurashige | G02B 27/48 353/85 |
| 2014/0152530 | A1* | 6/2014 | Venkatesha | G01B 11/00 345/8 |
| 2014/0375965 | A1* | 12/2014 | Suzuki | G03B 21/16 353/57 |
| 2016/0234485 | A1* | 8/2016 | Robbins | H04N 13/0429 |

* cited by examiner

HEAD MOUNTED DISPLAY DEVICE

TECHNICAL FIELD

The invention relates to a head mounted display device (HMD) and particularly to head mounted displays comprising an optical module containing a light emitting source and an optical waveguide for guiding light emitted by the light emitting source to a wearer's eye.

DESCRIPTION OF RELATED ART

A head-mounted display is a displaying apparatus to be worn on the head in order to have information content directly displayed in front of one or each eye. HMDs are also known as near-to-eye displays.

An HMD can take various forms, including eyeglasses, visors, helmets, masks and goggles.

Generally, an HMD comprises an optical module with a light emitting source that generates light beams from an electronic signal, the light emitting source being generally of the miniature screen, laser diode, light-emitting diode type, organic light-emitting diodes or spatial light modulator. The HMD also comprises an optical waveguide for shaping light beams coming from the optical module and for directing light beams towards the wearer's eye to enable the visualisation of information content.

HMDs may be immersive or non immersive (with see through or see around mechanisms). With respect to non immersive HMDs, two light paths lead to the wearer's retina: the display image path taken by light beams emitted by an optical module of the HMDs and the scene image path taken by light beams coming from the environment of the wearer.

Thus, the wearer's eye receives natural light from the environment as well as artificial light, the spectrum of which differs from that of natural light.

The human eye can see wavelengths within a range of about 380 nm to about 780 nm. Within this visible light spectrum, some wavelengths can induce acute or cumulative photo-damage to the eye, while other wavelengths are necessary to synchronize human biological rhythms. The beneficial effects of specific light on biological rhythms may be used in the field of Chronobiology.

Light therapy or phototherapy consists of exposure to light, daylight, or artificial light, with a specific spectrum and/or with a specific light radiance, for a prescribed amount of time and, in some cases, at a specific time of day. Light therapy through the eyes may be used to treat circadian rhythm disorders, such as delayed sleep phase disorder, and can also be used to treat seasonal affective disorder, with some support for its use also in non-seasonal psychiatric disorders.

Indeed, photons received by the eye are useful to control many non-visual biological functions. These non-visual biological functions, also referred to as non-visual irradiance detection tasks, are triggered by a third photoreceptor, the intrinsically photosensitive retinal ganglion cells (ipRGC) using melanopsin associated pigment. Non-visual photoresponse is essential for circadian entrainment in many non-visual functions, encompassing sleep/wake state (melatonin synthesis), pupil light reflex, cognitive performance, mood, locomotor activity, memory, body temperature, etc.

Consequently, a suitable see-through head mounted display system emitting light can have many applications, for example in mitigating the effects of jet-lag, sleep disorders, etc.

Therefore, there is a need for an efficient and reliable head mounted display device providing an efficient phototherapy treatment.

SUMMARY

Thus, one object of the present invention is to provide a head mounted display device which is efficient and safe for the wearer while allowing for simultaneous vision and light therapy.

To this end, the invention proposes a head mounted display device comprising:
- a light emitting source,
- an optical waveguide adapted to collect light emitted from the light emitting source and to guide the collected light to the eye of a wearer when the head mounted display device is being worn by the wearer, and
- a controller device adapted to control the emitted spectrum and/or radiance and/or light level emitted by the light emitting source.

Advantageously, the wearer of such a device can continue his activities during the light therapy session.

Such light therapy can be useful for chronobiological regulation and synchronization, myopia prevention or reduction, and/or for some people with epilepsy for an epilepsy palliative treatment.

Moreover, such a light therapy session has no compromise on vision for the user: there is no direct light emission onto the eye, thereby avoiding glare and dazzling.

Furthermore, a more efficient light therapy treatment is obtained thanks to a homogeneous and controlled exposure of the retina of the eye and particularly to an accurate control of the focus and the intensity of the light reaching the retina of the eye.

Furthermore, only a narrow spectral range of wavelengths can advantageously be emitted by the light source to provide both an efficient phototherapy treatment within the blue-turquoise/green ranges, while having no damaging effect on the retina i.e. no emission of noxious blue-violet light.

According to further embodiments which can be considered alone or in combination:
- the head mounted display device further comprises an optical sensor adapted to detect the light level and/or spectrum of the ambient light, and the controller device is configured so as to control the light emitting source based at least on the detected light level and/or spectrum of the ambient light;
- the controller device is configured so as to control the light emitting source based on at least one of:
  - the day time,
  - the geo-localization of the head mounted display device, and
  - wearer data relating to the age of the wearer and/or the biological clock of the wearer and/or the activity of the wearer and/or ocular disease of the wearer and/or the type of physiological disorder of the wearer;
- the controller device is configured so as to provide gradient irradiances;
- the controller device is configured so as to provide spatially modulated irradiances;
- the head mounted display device further comprises an eye tracking device adapted to detect position and/or movement of the eye of the wearer, and the controller device is configured so as to control the light emitting source based at least on the detected position and/or movement of the eye of the wearer;

the optical waveguide comprises refractive optics, for example mirrors, prism combiner, semi-reflective diopter, light guide optical element (LOE);

the optical waveguide comprises diffractive optics, for example embedded grating and/or holographic optical elements;

the optical waveguide comprises Fourier optics;

the optical waveguide comprises multiplexed beam splitters;

the light emitting source comprises one or several colored LEDs, for example blue-green and/or amber LEDs;

the head mounted display device further comprises an optical lens mounted in a spectacle frame;

the controller device is configured so as to provide chronobiology regulation and synchronization and/or affective disorders regulation and/or myopia prevention or reduction and/or epilepsy palliative treatment by controlling the light emitting source to provide emission between 460 nm and 520 nm with specific spatial and temporal patterns;

the head mounted display device has a spectral transmission profile having an average transmittance Ta between 380 nm and 780 nm and an average red light transmittance Tr between a first limit L1 and a second limit L2, with Tr<2*Ta/3 and L1=600 nm and L2=780 nm;

L2=650 nm;

Tr<Ta/5;

the spectral transmission profile has an average blue light transmittance Tb between a third limit L3 and a fourth limit L4, with Tb<2*Ta/3, for example Tb<Ta/5, with L3=380 nm and L4=455 nm;

Tr is substantially equal to Tb;

the average transmittance Ta between 380 nm and 780 nm is greater than or equal to 50%;

the head mounted display device is configured to selectively and substantially reflect light arriving on the front face of the head mounted display device between L1 and L2 and/or L3 and L4;

the head mounted display device comprises an interferential filter;

the head mounted display device is a photonic crystal optical filter;

BRIEF DESCRIPTION OF THE DRAWINGS

Embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION OF THE PREFERRED EMBODIMENTS

Figure 1:
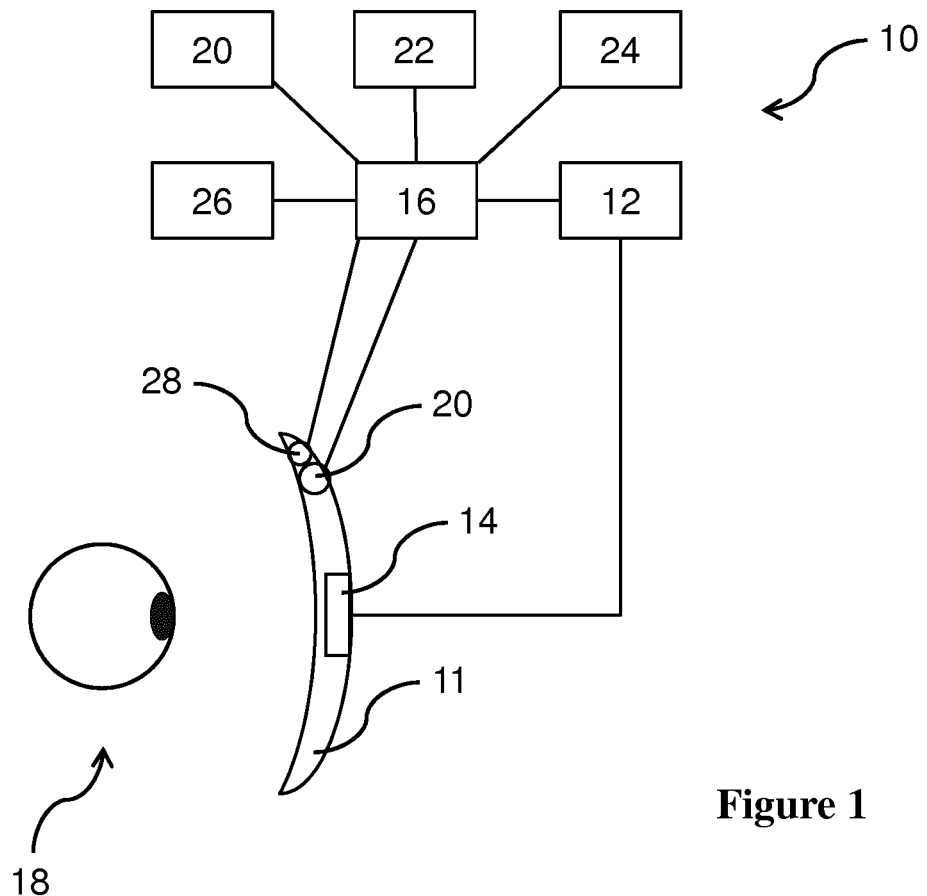
FIG. 1 is a schematic block diagram representing an eye of a wearer and a head mounted display device according to an embodiment of the invention.
Figure 2:
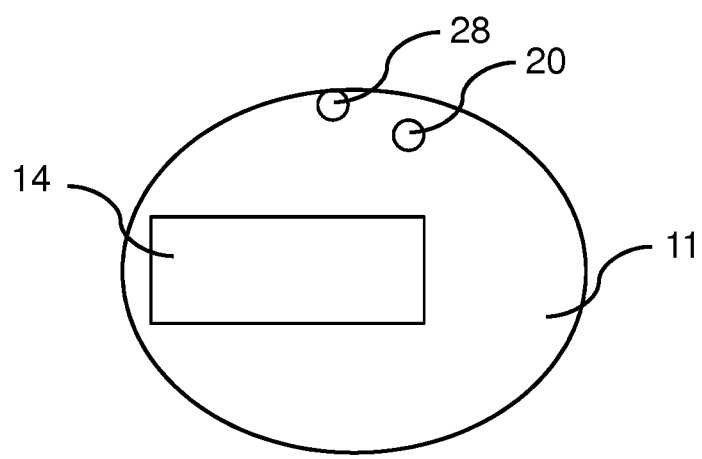
FIG. 2 is an illustration of a face of the lens of the head mounted display device of the FIG. 1.

FIG. 1 illustrates an eye of a wearer and a head mounted display device according to an embodiment of the invention.

According to several embodiments, the head mounted display device may be a non-immersive device (see through or see around head mounted display device) or an immersive device.

The head mounted display device 10 according to the invention is advantageously housed in the form of eye-glasses. The housing has a spectacle frame defining the shape of the eye-glasses. Preferably, the head mounted display device 10 further comprises at least an optical lens 11 mounted in the spectacle frame and designed to be placed in front of a corresponding eye 18 of the wearer.

The head mounted display device 10 according to the invention comprises an optical module comprising a light emitting source 12, an optical waveguide 14 and a controller device 16.

In one embodiment, the light emitting source can comprise a plurality of colored light-emitting diodes (LED), for example and preferably:

a blue-green LED having a central emission wavelength comprised between 460 nm to 520 nm, and In another embodiment, the light emitting source can further comprise a plurality of amber LED having a central emission wavelength comprised between 550 and 590 nm In an alternative embodiment, the blue-green LED can be replaced by a green LED having a central emission wavelength at around 510 nm.

The optical waveguide 14 is adapted to collect light emitted from the light emitting source 12 and to guide the collected light to the eye 18 of a wearer when the head mounted display device 10 is being worn by the wearer.

The optical waveguide 14, adapted to collect light emitted and to guide it to the eye 18 of the wearer, can comprise refractive optics, diffractive optics, Fourier optics and/or multiplexed beam splitters.

Refractive optics can be for example mirrors, prism combiner, semi-reflective dioptre and/or light-guide optical element (LOE).

Diffractive optics can be for example embedded grating and/or holographic optical elements.

The controller device 16 is adapted to control the emitted spectrum and/or radiance and/or light level emitted by the light emitting source 12.

Furthermore, the controller device 16 can be configured so as to provide gradient irradiances and/or spatially modulated irradiances. Thus, the exposure of the retina of the eye can be homogeneous and/or controlled allowing advantageously a better efficacy of a light treatment.

Advantageously, the head mounted display device according to the invention allows a simultaneous control of light properties: spatial distribution, directivity, intensity and spectrum of the light reaching the retina of the eye of the wearer.

Preferably, the illumination of the eye is peripheral in order to reduce the perception of the light treatment. Thus, the incidence angles of the light emitted by the light emitting source 12 and from the optical waveguide 14 are defined taking advantage of the Stiles-Crawford effect with peripheral incidence angles and of the cone density and distribution within the retina.

Controlling the direction and the diffusing angle of the light entering the pupil of the eye and reaching the retina provides a better focus of the light and a better intensity control of the light reaching the eye.

Moreover, the controller device 16 can be configured so as to provide a personalized retinal exposure for a wearer with, for example, a specific emitted colour in front of the eye. Thus the pattern of excitation light can be changed for example for epileptic people.

Advantageously, the light emitting source 12 and the controller device 16 are housed in the spectacle frame and in particular, in a sidepiece of the spectacle frame.

Preferably, the optical waveguide 14 can be embedded in or mounted in front of the optical lens 11.

Furthermore, the head mounted display device 10 comprises preferably at least one optical sensor 20 arranged to measure data relating to an incident light on the head mounted device 10 such as the ambient light.

The optical sensor 20 is adapted to measure the light level and/or spectrum of the ambient light.

The optical sensor 20 can be arranged in front of and/or behind the optical lens.

The optical sensor 20 may be positioned outwardly to see the real scene without alteration by the optical lens 11. Nonetheless, it may be disposed directly on the front face of the optical lens 11 as well as accommodated in the optical lens.

The controller device 16 is configured so as to control the light emitting source 12 based at least on the measured light level and/or spectrum data of the incident/ambient light.

More particularly, the optical sensor 20 may be:
a micro-spectrometer
a photodiode array, each photodiode with a specific bandwidth allowing the detection of particular light frequency
a camera for complete real scene analysis or special object detection, like high luminance object
more specialized sensor(s), for example for accurately detecting a light level, intensity and/or a wavelength to be eliminated.

The optical sensor 20 is in communication with the controller device 16 with a wired or wireless connection. This connection may further involve a sensor interface detailed below.

Advantageously, the controller device 16 is also configured so as to control the light emitting source 12 based on the day time and/or on the geo-localization of the head mounted display device 10. To this end, the head mounted display device 10 further comprises a real time clock 22 and/or a global positioning system (GPS) 24. The head mounted display device 10 can also comprise a sensor adapted for controlling the wearing time of the head mounted display device.

Indeed, the controller device 16 can control the start and/or the end of the light therapy or the retinal exposure duration of the light therapy.

The controller device 16 may comprise processing means 41. These latter components are not detailed, but may be any of common components used to design electronic systems, such as for example STM32 or Kinetis microcontroller or iMX6 processor. The controller device 16 may also comprise interfacing means. For instance, the sensor interface may allow the controller device 16 to functionally interface the optical sensor 20.

The interfacing means are not detailed, but may be any of common interfaces used to design electronic systems, such as for example I$^2$C bus, Mipi interface, or any wired or wireless communication between components.

The controller device 16 may further comprise data storing means, for instance for storing measured and/or collected data. These latter are not detailed, but may be any of common non-transitory storage medium used to design electronic systems, such as for example SRAM memory, Flash memory, etc.

The controller device 16 may further comprise supplementary sensors or be communicatively connected to such supplementary sensors with these latters being or not comprised in some external devices. The supplementary sensors are not detailed, but may be any kind of touch sensors, pressure sensors, light sensors, temperature sensors, chronometers, displacement sensors, accelerometers, gyroscopes, magnetometers, or actimetry sensors. Thus, in particular embodiments, a displacement sensor may be used to automatically detect an activity (walking, running, standing or sitting). Other sensors (temperature, blood pressure, etc.) may also be used.

Wireless connection of the controller device 16 to an external processor is also possible; thus the management of the head mounted device 10 may be made by the use of the external processor and the control unit 16 advantageously needs less processing resources. The decision and way to activate the head mounted device 10 may be determined locally (on or near the head mounted device 10) or remotely (on the external device).

Said external devices or external processors may comprise a mobile phone, a smartphone, a control pad, an iPad, tablet, or a graphics pad. These devices or processors may get supplementary information about the environment of the device 10 and, if appropriate, the wearer (activity, health test, agenda, etc.), in order for the controller device 16 to take into account at least one of these supplementary information or measured data in controlling the light emitting source 12.

Wireless connection of the controller device 16 to the Internet is also possible, for instance via the external devices. In such a case, regulation may be done with information about the wearer and his environment coming from the Internet, and the management of the head mounted device may be performed by a remote controller comprised in an Internet server.

In a preferred embodiment, the head mounted display device 10 further comprises an eye tracking device 28 adapted to detect position and/or movement of the eye 18 of the wearer. In the case of this preferred embodiment, the controller device 16 is configured so as to control the light emitting source 12 based at least on the detected position and/or movement of the eye of the wearer. The eye tracking device 28 can be arranged in front of and/or behind the optical lens 11.

Moreover, the controller device 16 can also be configured so as to personalize or control the light emitting source 12 based on a wearer profile defined by wearer parameters.

Such wearer parameters are related to the age of the wearer and/or the biological clock of the wearer and/or the activity of the wearer (working activity, sport activity, etc. . . . ) and/or ocular disease of the wearer and/or the type of physiological disorder of the wearer.

Such wearer data can be stored in the data storing means on a memory 26.

In one embodiment, such a memory 26 may be integrated in the head mounted display device 10 and housed in the frame.

Thus, such a head mounted display device 10 allows a personalized management of the emitted light by the light emitting source 12 according to the wearer profile.

Furthermore, the controller device 16 can be configured so as to provide chronobiology regulation and/or affective disorders regulation and/or myopia reduction and/or prevention and/or epilepsy palliative treatment by controlling the light emitting source 12 to provide emission in a selected range of wavelengths between 460 nm and 520 nm with specific spatial and temporal patterns.

The head mounted display device according to the invention is configured to selectively emit light in at least one selected range of wavelengths of light in the visible spectrum of 460 nm to 520 nm, preferably of 480 nm to 520 nm (herewith defined as the selected range of wavelengths of light or chronobiological blue light).

In preferred embodiments, the selected range of wavelengths of light is centered on a wavelength within the range 480 nm to 510 nm with a bandwidth from 20 nm to 70 nm.

In a first preferred exemplary embodiment, the range of wavelengths is centered on a wavelength of substantially 480 nm with a bandwidth from 20 nm to 40 nm.

In a second preferred exemplary embodiment, the range of wavelengths is centered on a wavelength of substantially 490 nm with a bandwidth from 20 nm to 40 nm.

In operation, light from the light emitting source 12, preferably having a wavelength ranging from 460 nm to 520 nm, is launched into one end of the optical waveguide 14. The light emitting source 12 is controlled by the controller device 16 for modulating the emitted spectrum, the light intensity, the exposure time and duration preferably according to wearer parameters stored in the memory and according to date and time.

Moreover, the light emitting source 12 can be activated for example if the incident light received during the day and measured by at least the optical sensor 20 is less than a threshold predetermined according to wearer parameters.

The head mounted display device according to the invention results in an increase of the retinal exposure to the selected range of wavelengths within the blue-green range. The selected range of wavelengths is the best synchronizer of human non-visual biological functions.

The inventors have evidenced in a clinical study led in 2013 on 52 young healthy subjects that showed 2-weeks of continuously wearing optical filters that cut off more than 99% of wavelengths comprised between 460 nm and 520 nm is sufficient to induce a 1 hour shift in L5 (five least active hours) and M10 (10 most active hours) sleep-wake criteria.

By optimizing retinal light reception in between 460 nm and 500 nm, we induce the direct stimulation of ipRGC by melanopsin photoreception peaking at 480 nm for humans.

By taking into account the poor spatial density of ipRGC (only 1 to 3% of retinal ganglion cells) compared to that of rod photoreceptors, the probability of absorbing a photon is more than 1 million times lower of a given area of photostimulation. Thus, even if ipRGC phototransduction cascade is highly amplified, the inventors suspect that ipRGCs receive additional input from a complementary photoreception process involving rods. We have observed that ipRGCs may be responsive to lower levels of illumination than initially planned, confirming the role of rods. By extending the transmitted spectral range to 460-520 nm, we induce both the direct stimulation of ipRGC and the indirect stimulation by the incoming rod driven signals peaking near 500 nm.

In particular, this specific illumination range is the most potent stimulus for entraining endogenous rhythms to the daily light cycle with the two photoreceptive processes involved: the melanopsin-driven phototransduction mechanism within the ipRGC itself, peaking near 480 nm and indirect photoreception in rods, peaking near 500 nm.

Therefore, head mounted display devices according to embodiments of the invention may be used in therapy and/or disease prevention.

Such device according to the invention may be used in therapy for treatment of subjects suffering from chronobiological disorders such as circadian rhythm sleep disorders, sleep disorders, pupil dilation, jet lag, delayed and advanced sleep phase syndromes, mood disorders, seasonal affective disorder such as depression or fatigue, postpartum depression, cancer risks, hormonal disorders, alertness disorders and cognitive performances, appetite and obesity, memory disorders, psychomotor disorders, body temperature deregulation, premenstrual disorders, epilepsy crisis and myopia. The device can help shift workers to adjust their biological clock to a new shift.

Indeed, the device according to the invention can compensate inadequate lighting conditions (lack of beneficial blue at specific moments) to help the biological clock to remain synchronized through the good blue/melatonin secretion relationship.

The present invention provides also a method to treat circadian rhythm sleep disorders comprising selectively allowing retinal exposure of an eye to at least one selected range of wavelengths of light in the visible spectrum of 460 nm to 520 nm, preferably of 480 nm to 520 nm.

In an embodiment, as already discussed, such device according to the invention may be used in therapy for treatment of subjects suffering from epilepsy. Recent research suggests that some forms of epilepsy and depression are bi-directional conditions, which suggests that light therapy could be an effective treatment for some people with epilepsy. Endogenous melatonin production seems to have an influence on seizure thresholds for patients with temporal lobe epilepsy. Besides, bright blue-green light is largely involved in the endogenous production and regulation of melatonin. Thus, we can hypothesize that bright blue-green light is involved to some extent in modulation of seizure thresholds. For people suffering from lobe temporal epilepsy, light may help smooth out some of the seasonal peaks in seizure frequencies.

In an embodiment, as already discussed, such device according to the invention may be used in myopia prevention and/or reduction. An adapted light therapy may contribute to reduce the risk of myopia onset by acting positively on the production cycle of dopamine. Dopamine is a retinal neurotransmitter associated with light adaptation. Dopamine has an impact on the eye length and thus on myopia. Recent research shows that dopaminergic cells are linked to intrinsically photosensitive retinal ganglion cells and that they are regulated by the chronobiological blue light at around 480 nm. This specific light may activate endogenous dopamine production, while a lack of this light (spectrum and/or light level) may inhibit dopamine production. The inhibition may in the long term contribute to the elongation of the eye.

In an embodiment, the head mounted display device has a spectral transmission profile having an average transmittance Ta between 380 nm and 780 nm and an average red light transmittance Tr between a first limit L1 and a second limit L2 with Tr<2*Ta/3 and L1=600 nm and L2=780 nm.

According to an embodiment of the invention, L2 may be equal to 700 nm and Tr<Ta/2.

According to an embodiment of the invention, L2 may be equal to 650 nm and Tr<Ta/5.

In the sense of the invention the "average transmittance" over a given range of wavelengths ($\lambda_1$, $\lambda_2$) corresponds to $\int_{\lambda_1}^{\lambda_2} T(\lambda)d\lambda$, with $T(\lambda)$ the transmittance of the head mounted display device as a function of the wavelength. The transmittance corresponds to the fraction of incident light that is transmitted through the head mounted display device.

The average transmission Ta of the head mounted display device between 380 nm and 780 nm is greater than or equal to 50%.

According to an embodiment, the head mounted display device is configured to have an average transmittance Ta between 380 nm and 780 nm from 3% to 43% (i.e. at an inhibition rate of 97% to 57%) for example depending on the level of solar protection required such as class 0 to 4 as defined by the International standards such as NF EN 1836+A1_2007E or ISO_DIS 12312-1 E.

More precisely, the average transmittance Ta could be:
greater than or equal to 18% and smaller than or equal to 43%, so as to provide an device adapted for average luminosity environments, or
greater than or equal to 8% and smaller than or equal to 17%, so as to provide article device adapted for high luminosity environments, or
greater than or equal to 3% and smaller than or equal to 8%, so as to provide an optical article device adapted for very high luminosity environments.

In another embodiment, the head mounted display device is configured to have an average transmittance in the visible spectrum comprised between 80% and 100% (i.e. at an inhibition rate of 20% to 0%).

Additionally, the head mounted display device of the invention may be used in protecting at least part of an eye of a user from harmful ultraviolet light and/or harmful blue light.

Indeed, the head mounted display device may have a spectral transmission profile having an average blue light transmittance Tb between a third limit L3 and a fourth limit L4, with Tb<2*Ta/3, for example Tb<Ta/5, with L3=380 nm and L4=455 nm.

According to an embodiment of the invention the average red light transmission Tr over L1 and L2 is substantially equal to the average blue light transmission Tb over between L3 and L4.

According to an embodiment of the invention, the head mounted display device is configured to selectively and substantially reflect light arriving on the front face of the head mounted display device, i.e. the incident light, with wavelengths comprised between L1 and L2 and/or L3 and L4.

So as to selectively and substantially reflect light, the head mounted display device according to the invention may comprise an interferential filter.

In an exemplary embodiment, the interferential filter is an interferential coating.

As used herein, the term coating is understood to mean any layer, layer stack or film which may be in contact with the uncoated substrate, generally with two main faces corresponding in the finished ophthalmic lens to the front and rear faces thereof, and/or with another coating, for example a sol-gel coating or a coating made of an organic resin. A coating may be deposited or formed through various methods, including wet processing, gaseous processing, and film transfer. The functional coatings classically used in optics may be, without limitation, an impact-resistant and/or adhesion primer, an abrasion-resistant and/or scratch-resistant coating, an anti-reflection coating, an antistatic coating, an anti-soiling coating, an anti-reflective coating, an anti-smudge coating, an anti-dust coating, an anti-fog coating, a water repellent coating, an anti-scratch coating, an interferential filter, a tinted coating, a mirror coating, a photochromic coating, and a combination of any of preceding compatible coatings, especially an impact-resistant primer coating coated with an abrasion and/or scratch-resistant coating.

The interferential filter may be manufactured using interferential technologies such as dielectric multi-layers with variable optical refractive indexes, photonic band gap materials such as liquid cristal technology, cholesteric crystals or MOF technology, or holographic gratings and any combination thereof.

In exemplary embodiments, the interferential filter may be coated on the front face of the head mounted display device such as any functional coating, e.g. anti-reflection coating, mirror coating or can be applied onto a functional coating thanks to various methods as those disclosed for the incorporation of luminescent agents described in greater details further in the description and known form the state of art.

In one exemplary embodiment of the invention, the interferential coating of the front face of the head mounted display device may comprise a stack of layers of dielectric materials with a combination of layers of high refractive index (HI, n>1.5), and layers of low refractive index (LI n≤1.5) configured to define the spectral reflectance profile according to the invention.

In one embodiment, the optical filter may be obtained through a photonic crystal optical filter in order to define the desired spectral transmission profile according to the invention.

The photonic crystal optical filter may be manufactured using photonic band gap materials.

It should be noted that the optical filter may be configured as a passive system or an active system. By passive system it is understood that the optical filter presents a filtering function which cannot be modified or changed. By active system, it is understood that the optical filter present at least a function that can be modified or changed by an external stimulation such as energy, actinic radiation, heating, etc. so that transmission of the selected range of wavelength of light may be switched on or off, or the light transmittance factor varied according to the time of day or the activity of the wearer or the exposure to light.

The device combines two optical approaches for light management: a red filtering and a blue-green light emission.

Indeed, the device combines both actions of:
light emission in the selected range of wavelengths for hormonal regulation, in particular regulation of dopamine which is implied in eye length, and
selective red light filtering to deal with the chromatic effect suspected in myopia Advantageously, combining light therapy with red light filtering may be used to minimize or prevent from progressive myopia.

The invention claimed is:

1. A head mounted display device comprising:
a light emitting source;
an optical waveguide configured to collect light emitted from the light emitting source and to guide the collected light to an eye of a wearer when the head mounted display device is being worn by the wearer; and
a controller configured to control the light emitting source to modulate at least one of an emitted spectrum, a radiance, and a light level of light emitted by the light emitting source, wherein
the controller is configured to provide at least one of a chronobiology regulation, a chronobiology synchronization, an affective disorders regulation, a myopia prevention, a myopia reduction and epilepsy palliative treatment, by controlling the light emitting source to provide light emission between 460 nm and 520 nm, with the emitted light having spatial and temporal patterns.

2. The head mounted display device according to claim 1, further comprising an optical sensor configured to detect at least one of a light level of an ambient light and spectrum of the ambient light, and wherein the controller is configured to control the light emitting source based at least on at least one of the detected light level, radiance and the spectrum of the ambient light.

3. The head mounted display device according to claim 1, wherein the controller is configured to control the light emitting source based on at least one of:
   a day time;
   a geo-localization of the head mounted display device; and
   wearer data relating to at least one of an age of the wearer, a biological clock of the wearer, an activity of the wearer, an ocular disease of the wearer, and a type of a physiological disorder of the wearer.

4. The head mounted display device according to claim 1, wherein the controller is configured to control the light emitting source to provide gradient irradiances for the light emitted by the light emitting source.

5. The head mounted display device according to claim 1, wherein the controller is configured to control the light emitting source to provide spatially modulated irradiances for the light emitted by the light emitting source.

6. The head mounted display device according to claim 1, further comprising an eye tracking device configured to detect at least one of a position and movement of the eye of the wearer, and wherein the controller is configured to control the light emitting source based at least on at least one of the detected position and movement of the eye of the wearer.

7. The head mounted display device according to claim 1, wherein the optical waveguide comprises refractive optics.

8. The head mounted display device according to claim 1, wherein the optical waveguide comprises diffractive optics.

9. The head mounted display device according to claim 1, wherein the optical waveguide comprises Fourier optics.

10. The head mounted display device according to claim 1, wherein the optical waveguide comprises multiplex beam splitters.

11. The head mounted display device according to claim 1, wherein the light emitting source comprises one or more colored light emitting devices (LEDs).

12. The head mounted display device according to claim 1, further comprising an optical lens mounted in a spectacle frame.

13. The head mounted display device according to claim 1, having a spectral transmission profile having an average transmittance $Ta$ between 380 nm and 780 nm and an average red light transmittance $Tr$ between a first limit $L1$ and a second limit $L2$, with $Tr<2*Ta/3$, $L1=600$ nm, and $L2=780$ nm.

14. The head mounted display device according to claim 13, wherein $L2=650$ nm.

15. The head mounted display device according to claim 14, wherein $Tr<Ta/5$.

16. The head mounted display device according to claim 13, wherein the spectral transmission profile has an average blue light transmittance $Tb$ between a third limit $L3$ and a fourth limit $L4$, with $Tb<2*Ta/3$.

17. The head mounted display device according to claim 13, wherein the head mounted display device is configured to selectively emit light in a selected range of wavelengths of light centered on a wavelength within the range of 480 nm to 510 nm, with a bandwidth in a range from 20 nm to 70 nm.

18. The head mounted display device according to claim 7, wherein the refractive optics comprises at least one of a prism combiner, a semi-reflective diopter, and a. light guide optical element.

19. The head mounted display device according to claim 16, wherein $Tb$ is $<Ta/5$, wherein $L3$ is 380nm, and wherein $L4$ is 455 nm.

* * * * *